(12) United States Patent  
Savall et al.

(10) Patent No.: US 11,806,104 B2
(45) Date of Patent: *Nov. 7, 2023

(54) INTERLOCK MECHANISMS TO DISENGAGE AND ENGAGE A TELEOPERATION MODE

(71) Applicant: Verb Surgical Inc., Santa Clara, CA (US)

(72) Inventors: Joan Savall, Palo Alto, CA (US); Denise Ann Miller, Scotts Valley, CA (US); Anette Lia Freiin von Kapri, Mountain View, CA (US); Paolo Invernizzi, Milan (IT); John Magnasco, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/725,351

(22) Filed: Apr. 20, 2022

(65) Prior Publication Data

US 2022/0323168 A1    Oct. 13, 2022

Related U.S. Application Data

(63) Continuation of application No. 16/415,992, filed on May 17, 2019, now Pat. No. 11,337,767.

(51) Int. Cl.
*A61B 34/35* (2016.01)
*G06F 3/01* (2006.01)
(Continued)

(52) U.S. Cl.
CPC .............. *A61B 34/35* (2016.02); *A61B 34/25* (2016.02); *B25J 9/0009* (2013.01); *B25J 9/1689* (2013.01);
(Continued)

(58) Field of Classification Search
CPC ........... A61B 2017/00212; A61B 2017/00216; A61B 2034/305; A61B 34/25;
(Continued)

(56) References Cited

U.S. PATENT DOCUMENTS 7,865,266 B2    1/2011    Moll et al.
8,831,782 B2    9/2014    Itkowitz
(Continued)

FOREIGN PATENT DOCUMENTS

EP             3395251      10/2018
KR      10-1802464 B1      11/2017
(Continued)

OTHER PUBLICATIONS

Teleoperation through Eye Gaze (TeleGaze): A Multimodal Approach, by Hemin Omer Latif, Nasser Sherkat and Ahmad Lotfi; Published in: 2009 IEEE International Conference on Robotics and Biomimetics (ROBIO); 2009; 6 Pages.
(Continued)

*Primary Examiner* — Kathleen M Walsh
(74) *Attorney, Agent, or Firm* — Aikin & Gallant, LLP (57) ABSTRACT

A method for engaging and disengaging a surgical instrument of a surgical robotic system comprising: receiving a plurality of interlock inputs from one or more interlock detection components of the surgical robotic system; determining, by one or more processors communicatively coupled to the interlock detection components, whether the plurality of interlock inputs indicate each of the following interlock requirements are satisfied: (1) a user is looking toward a display, (2) at least one or more user interface devices of the surgical robotic system are configured in a usable manner, and (3) a surgical workspace of the surgical robotic system is configured in a usable manner; in response to determining each of the interlock requirements are satis-
(Continued)

fied, transition the surgical robotic system into a teleoperation mode; and in response to determining less than all of the interlock requirements are satisfied, transition the surgical robotic system out of a teleoperation mode.

19 Claims, 5 Drawing Sheets

(51) Int. Cl.
    *A61B 34/00* (2016.01)
    *B25J 9/00* (2006.01)
    *B25J 9/16* (2006.01)
    *A61B 34/30* (2016.01)
(52) U.S. Cl.
    CPC .............. *G06F 3/012* (2013.01); *G06F 3/013* (2013.01); *G06F 3/017* (2013.01); *A61B 2034/305* (2016.02)
(58) Field of Classification Search
    CPC ......... A61B 34/30; A61B 34/35; A61B 34/37; A61B 34/74; A61B 90/03; B25J 9/0009; B25J 9/1689; G06F 3/012; G06F 3/013; G06F 3/017
    USPC ........................................................ 606/130
    See application file for complete search history.

(56) References Cited

U.S. PATENT DOCUMENTS

| | | | |
|---|---|---|---|
| 9,314,306 B2 | 4/2016 | Yu | |
| 9,360,934 B2* | 6/2016 | Ruiz Morales | G06F 3/04847 |
| 9,699,445 B2 | 7/2017 | Hoffman et al. | |
| 9,901,402 B2 | 2/2018 | Itkowitz et al. | |
| 9,925,662 B1 | 3/2018 | Jules et al. | |
| 10,251,713 B2* | 4/2019 | Ruiz Morales | G06F 3/0482 |
| 10,895,757 B2* | 1/2021 | Fuerst | A61B 34/35 |
| 10,980,610 B2 | 4/2021 | Rosenberg et al. | |
| 11,204,640 B2* | 12/2021 | Freiin von Kapri | A61B 34/30 |
| 11,224,489 B2* | 1/2022 | Ruiz Morales | G06V 40/19 |
| 11,333,899 B2* | 5/2022 | Fuerst | H04N 13/383 |
| 11,337,767 B2* | 5/2022 | Savall | G06F 3/012 |
| 11,478,318 B2* | 10/2022 | Cone | B25J 13/04 |
| 2009/0315827 A1 | 12/2009 | Elvesjo et al. | |
| 2011/0118748 A1 | 5/2011 | Itkowitz | |
| 2012/0071892 A1 | 3/2012 | Itkowitz et al. | |
| 2012/0078080 A1 | 3/2012 | Foley et al. | |
| 2014/0024889 A1* | 1/2014 | Xiaoli | G06F 3/013 600/102 |
| 2015/0080909 A1 | 3/2015 | Itkowitz et al. | |
| 2015/0314447 A1* | 11/2015 | Zhang | B25J 9/1689 901/46 |
| 2016/0242860 A1 | 8/2016 | Diolaiti et al. | |
| 2016/0361125 A1 | 12/2016 | Balicki et al. | |
| 2017/0172675 A1* | 6/2017 | Jarc | A61B 34/35 |
| 2018/0016110 A1 | 1/2018 | Nobe et al. | |
| 2018/0036088 A1 | 2/2018 | Kilroy et al. | |
| 2018/0078034 A1* | 3/2018 | Savall | A47B 21/04 |
| 2018/0078319 A1 | 3/2018 | Nobles et al. | |
| 2018/0092706 A1* | 4/2018 | Anderson | A61B 34/30 |
| 2018/0161108 A1 | 6/2018 | Savall et al. | |
| 2018/0280099 A1 | 10/2018 | Cone et al. | |
| 2018/0364810 A1 | 12/2018 | Parshionikar | |
| 2019/0076199 A1* | 3/2019 | Kline | G02B 7/002 |
| 2019/0231456 A1* | 8/2019 | Ruiz Morales | G06F 3/013 |
| 2019/0298481 A1* | 10/2019 | Rosenberg | G06F 3/013 |
| 2019/0328473 A1* | 10/2019 | Chassot | A61B 34/77 |
| 2020/0015918 A1* | 1/2020 | Payyavula | A61B 34/35 |
| 2020/0038124 A1* | 2/2020 | Lin | A61B 34/10 |
| 2020/0093367 A1 | 3/2020 | Dory et al. | |
| 2020/0222138 A1 | 7/2020 | Diolaiti | |
| 2020/0315721 A1 | 10/2020 | Rabindran et al. | |
| 2020/0360097 A1 | 11/2020 | DiMaio et al. | |
| 2020/0363868 A1* | 11/2020 | Freiin Von Kapri | A61B 34/30 |
| 2020/0390510 A1 | 12/2020 | Thompson et al. | |
| 2021/0088807 A1* | 3/2021 | Fuerst | H04N 13/383 |
| 2021/0145526 A1 | 5/2021 | Robinson et al. | |
| 2021/0145532 A1 | 5/2021 | Tucker et al. | |
| 2022/0179483 A1* | 6/2022 | Freiin von Kapri | G06F 3/013 |

FOREIGN PATENT DOCUMENTS

| | | |
|---|---|---|
| WO | 2018057814 | 3/2018 |
| WO | 2018/162921 A1 | 9/2018 |
| WO | 2018165047 | 9/2018 |
| WO | 2018195319 | 10/2018 |
| WO | 2018/217444 A2 | 11/2018 |

OTHER PUBLICATIONS

Robotic Technology in Surgery: Past, Present and Future, by David B. Camarillo, MS, Thomas M. Krummel, MD, and J. Kenneth Salisbury, Jr., PhD; 2004; 43 pages.
International Search Report & Written Opinion of the International Searching Authority dated Feb. 6, 2020 for PCT application No. US2019/034722.
International Preliminary Report on Patentability for International Application No. PCT/US2019/034722 dated Dec. 2, 2021, 9 pages.
Extended European Search Report for European Application No. 18945174.3 dated Oct. 27, 2022, 9 pages.
Final Office Action of the U.S Patent Office dated Feb. 22, 2022 for related U.S. Appl. No. 16/236,163.
Final Office Action of the U.S Patent Office dated May 25, 2021 for related U.S. Appl. No. 16/415,974.
Final Office Action of the U.S Patent Office dated May 3, 2021 for related U.S. Appl. No. 16/236,163.
International Preliminary Report on Patenlability for International Application No. PCT/US2019/034721 dated Dec. 2, 2021, 9 pages.
International Preliminary Report on Patentability for International Application No. PCT/US2019/068221 dated Jun. 16, 2021, 8 pages.
International Search Report & Written Opinion of the PCT Patent Office dated Feb. 3, 2020 for related PCT Patent Application. No. PCT/US2019/034721.
International Search Report and Written Opinion dated Sep. 23, 2019 for related PCT Appln. No. PCT/US2018/068221 18 Pages.
Jack Lloyd, How to Sync a PS3 Controller. Sep. 18, 2018, Accessed through https://www.wikihow.com/Sync-a-PS3-Controller (Year: 2018).
Non-Final of the U.S. Patent Office dated Jan. 12, 2021 for related U.S. Appl. No. 16/415,974.
Non-Final Office Action of the U.S. Patent Office dated Dec. 14, 2020 for related U.S. Appl. No. 16/236,163.
Non-Final Office Action of the U.S. Patent Office dated Oct. 6, 2021 for related U.S. Appl. No. 16/415,992.
Non-Final Office Action of the U.S. Patent Office dated Oct. 7, 2021 for related U.S. Appl. No. 16/236,163.
Notice of Allowance of the U.S. Patent Office dated Aug. 13, 2021 for related U.S. Appl. No. 16/415,974.
Notice of Allowance of the U.S. Patent Office dated Jan. 26, 2022 for related U.S. Appl. No. 16/415,992, dated Jan. 26, 2022, 8 pages.
Notice of Allowance of the U.S. Patent Office dated Jun. 10, 2022 for related U.S. Appl. No. 16/236,163.
Notice of Allowance of the U.S. Patent Office dated Mar. 18, 2022 for related U.S. Appl. No. 16/415,992.
Notice of Allowance of the USPTO dated Jan. 26, 2022 for related U.S. Appl. No. 16/415,792.

* cited by examiner

INTERLOCK MECHANISMS TO DISENGAGE AND ENGAGE A TELEOPERATION MODE

CROSS-REFERENCE TO RELATED APPLICATIONS

This application is a continuation of co-pending U.S. application Ser. No. 16/415,992 filed May 17, 2019, which is incorporated by reference herein.

FIELD

Embodiments related surgical robotic systems, are disclosed. More particularly, embodiments related to interlock mechanisms that disengage and engage a teleoperation mode, are disclosed.

BACKGROUND

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command a robotically-assisted tool located at an operating table. Such operation of a robotically-assisted tool remotely by a surgeon may be commonly referred to as teleoperation. For example, the surgeon may use a computer console located in the operating room, or it may be located in a different city, to command a robot to manipulate the surgical tool mounted on the operating table. The robotically-controlled surgical tool can be an endoscope mounted on a robotic arm. Accordingly, the surgical robotic system may be used by the remote surgeon to perform an endoscopic surgery.

The surgeon may provide input commands to the surgical robotic system, and one or more processors of the surgical robotic system can control system components in response to the input commands. For example, the surgeon may hold in her hand a user input device such as a joystick or a computer mouse that she manipulates to generate control signals to cause motion of the surgical robotic system components, e.g., an actuator, a robotic arm, and/or a surgical tool of the robotic system.

SUMMARY

During teleoperation with an open display in which the user can view their surroundings (as compared to a periscope type display) there is the possibility that the surgeon is looking away from the screen but still holding the user input devices that control the robotic tools. This introduces a risk since the surgeon could move the user input devices and unintentionally move the tools while not focusing on the screen. Therefore, in some aspects, the processes disclosed herein provide methods for determining whether a number of interlocks required for teleoperation are met, and therefore the user is looking at the open display (or an immersive display such as a periscope) and focused on teleoperation, such that teleoperation mode may be engaged or continue. In this aspect, the system detects a number of interlock parameters, conditions, inputs or the like, and then determines based on the detection of the interlock parameters, whether the system should disengage or engage teleoperation. In general, the interlock mechanisms or parameters are designed to determine the following (1) is the user looking at the screen, (2) is the user holding the user interface device in a usable manner, and (3) is the environment set up for teleoperation mode. If the answer to all of these conditions is yes, than teleoperation mode is engaged, if the answer to any of them is no, teleoperation mode may be disengaged.

Representatively, in one aspect, a method for engaging and disengaging a surgical instrument of a surgical robotic system is disclosed. The method may include receiving a plurality of interlock inputs from one or more interlock detection components of the surgical robotic system; determining, by one or more processors communicatively coupled to the interlock detection components, whether the plurality of interlock inputs indicate each of the following interlock requirements are satisfied: (1) a user is looking toward a display of the surgical robotic system, (2) at least one or more user interface devices of the surgical robotic system are configured in a usable manner, and (3) a surgical workspace of the surgical robotic system is configured in a usable manner; in response to determining each of the interlock requirements are satisfied, transition the surgical robotic system into a teleoperation mode in which the surgical instrument is controlled by at least one or more of the user interface devices; and in response to determining less than all of the interlock requirements are satisfied, transition the surgical robotic system out of a teleoperation mode such that the at least one or more user interface devices is prevented from controlling the surgical instrument. The user interface devices may include at least one of a handheld user input device and a foot pedal. The display may be an open display. The one or more interlock detection components may include at least one of an eye and/or head tracker, a tracking marker on a user's glasses, a tracking marker on a user's face mask, a chair swivel sensor, a chair pressure sensor, a headrest pressure sensor, an immersive display deployment sensor, a user interface device tracking sensor, a user interface device storage sensor, a user interface device contact sensor, or a transport sensor. In some aspects, the plurality of interlock inputs indicating a user is looking toward the display may include detecting a user gaze is toward the display; detecting a user head is rotated toward the display; detecting a chair associated of the surgical robotic system is facing the display; detecting a user is seated on the chair; and detecting the display is in a use position. In still further aspects, the plurality of interlock inputs indicating at least one or more user interfaces device of the surgical robotic system is configured in a usable manner may include detecting at least one user interface device is inside the surgical workspace; detecting an accurate user interface device location is received; and detecting at least one user interface device is being held by the user. In some cases, at least one of the plurality of interlock inputs indicating the surgical workspace of the surgical robotic system is configured in a usable manner may include detecting the surgical robotic system is not in a transportation configuration.

In another aspect, a method for disengaging a surgical instrument of a surgical robotic system is disclosed. The method may include determining, by one or more processors communicatively coupled to the surgical robotic system, that at least one interlock input previously received from one or more interlock detection components of the surgical robotic system is no longer present and therefore (1) a user is looking away from a display of the surgical robotic system, (2) at least one or more user interfaces device of the surgical robotic system is configured in a non-usable manner, or (3) a surgical workspace of the surgical robotic system is configured in a non-usable manner; and in response to determining that the interlock input is no longer present, transition the surgical robotic system out of a teleoperation mode such that a user interface device of the surgical robotic system is prevented from controlling a surgical instrument. In some aspects, determining the user is looking away from the display may include at least one of the following: detecting a user gaze is outside of the display; detecting a user head is rotated away from the display; detecting a chair associated of the surgical robotic system is facing away from the display; detecting a user is not seated on the chair; and detecting the display is in a non-use position. In some aspects, determining the surgical robotic system is configured in a non-usable manner may include at least one of the following: detecting at least one user interface device is outside a surgical workspace; detecting a received user interface device location is inaccurate; and detecting at least one user interface device is dropped by the user. In some aspects, determining the surgical workspace of the surgical robotic system is configured in a non-usable manner may include detecting the surgical robotic system is in a transportation configuration.

In still further aspects, a surgical robotic system is disclosed. The system may include a surgical instrument; a user console comprising a display, an interlock detecting component, and a user interface device; and one or more processors communicatively coupled to the interlock detecting component, the processors configured to: receive a plurality of interlock inputs from the interlock detecting component, wherein all of the plurality of interlock inputs are required for engagement of a teleoperation mode in which the surgical instrument is controlled by the user interface device; determine at least one of the plurality of interlock inputs received from the interlock detecting component is no longer present; and transition the surgical robotic system out of a teleoperation mode such that the user interface device is prevented from controlling the surgical instrument. In some aspects, the plurality of interlock inputs indicate each of the following interlock requirements are satisfied: (1) a user is looking toward a display of the surgical robotic system, (2) at least one or more user interfaces device of the surgical robotic system is configured in a usable manner, and (3) a surgical workspace of the surgical robotic system is configured in a usable manner. The interlock detecting component for detecting the plurality of interlocks indicating a user is looking toward a display may include: least one of an eye and/or a head tracker, a tracking marker on a user's glasses, a tracking marker on a user's face mask, a chair swivel sensor, a chair pressure sensor, a headrest pressure sensor or an immersive display deployment sensor. The interlock detecting components for detecting the interlocks indicating at least one or more user interface devices are configured in a usable manner may include: a user interface device tracking sensor, a user interface device storage sensor, or a user interface device contact sensor. The interlock detecting component for detecting the interlock indicating the surgical workspace may be configured in a usable manner comprises a transport sensor. In some aspects, the plurality of interlock inputs indicating a user is looking toward the display comprise: detecting a user gaze is toward the display; detecting a user head is rotated toward the display; detecting a chair associated of the surgical robotic system is facing the display; detecting a user is seated on the chair; and detecting the display is in a use position. In still further aspects, the plurality of interlock inputs indicating at least one or more user interfaces device of the surgical robotic system is configured in a usable manner comprise: detecting at least one user interface device is inside a surgical workspace; detecting an accurate user interface device location is received; and detecting at least one user interface device is being held by the user. In some aspects, at least one of the plurality of interlock inputs indicating the surgical workspace of the surgical robotic system is configured in a usable manner includes detecting the surgical robotic system is not in a transportation configuration.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Figure 1:
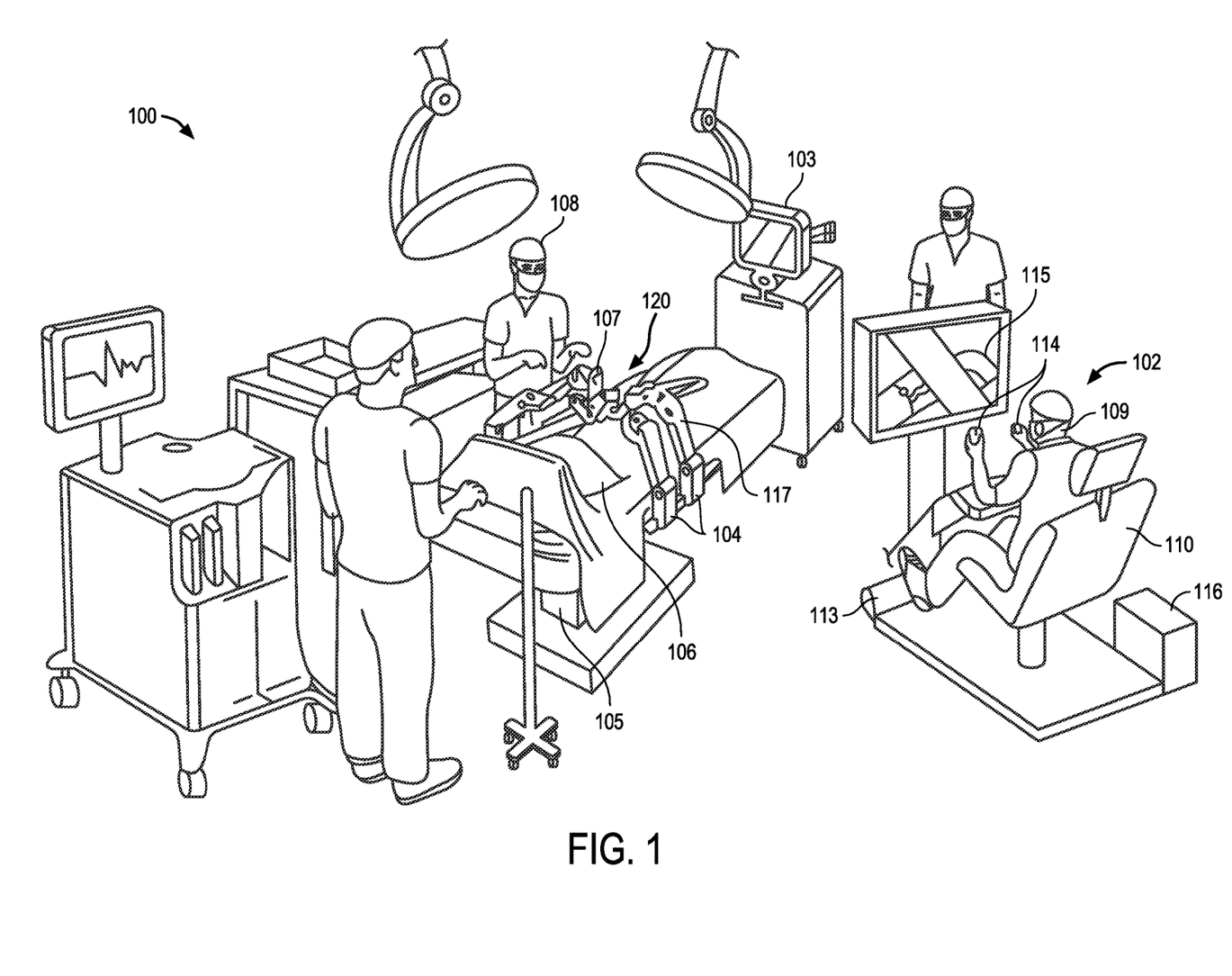
FIG. 1 is a pictorial view of an example surgical robotic system in an operating arena, in accordance with an embodiment.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilisation and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

In addition, in some aspects, surgical robotic system 100 may further include one or more interlock detecting mechanisms, devices, components or systems (e.g., trackers, sensors, etc), that can be used to determine whether a teleoperation mode should be engaged or, once engaged, should be disengaged. The interlock detecting mechanisms may detect, for example, whether a user is looking toward or away from the display 115, the UID is configured in a usable manner and/or the surgical environment is set up in a usable manner, and in turn, whether a teleoperation mode should be engaged or disengaged. For example, during a teleoperation mode of the surgical robotic system 100, in which the user is controlling the surgical tool 107 using the UID 114, the user should be viewing the tool movement on display 115. In some cases, however, the user may look away from the display 115 (intentionally or unintentionally) while still holding the UID 114 and controlling the surgical tool 107. This introduces a risk since the user could move the UID 114 and, in turn, unintentionally move the tool 107 while not focusing on the display 115. Surgical robotic system 100 may therefore further include interlock detecting mechanisms that can be used to determine whether the user is focused on the display 115, or otherwise interlocked or engaged with the system, in such a way that teleoperation mode is appropriate. The various interlock detecting mechanisms may be coupled to, in communication with, or otherwise associated with components of, the user console 102, and will be described in more detail in reference to FIG. 2.

It should be understood that "engaging" the teleoperation mode is intended to refer to an operation in which, for example, a UID or foot pedal that is prevented from controlling the surgical instrument, is transitioned to a mode (e.g., a teleoperation mode) in which it can now control the surgical instrument. On the other hand, disengaging the teleoperation mode is intended to refer to an operation which occurs when the system is in a teleoperation mode, and then transitioned to a mode (non-teleoperation mode) in which the UID or foot pedal can no longer control the surgical instrument. For example, teleoperation mode may be disengaged when the system determines that one or more of a number of interlocks required for teleoperation mode is no longer present or met. The interlocks required for teleoperation mode may correspond to user interactions with the user console that indicate the user is looking at, or otherwise focused on, the display, holding the controllers (e.g., UID) in a usable manner and/or the surgical environment is set up in a usable manner.

Figure 2:
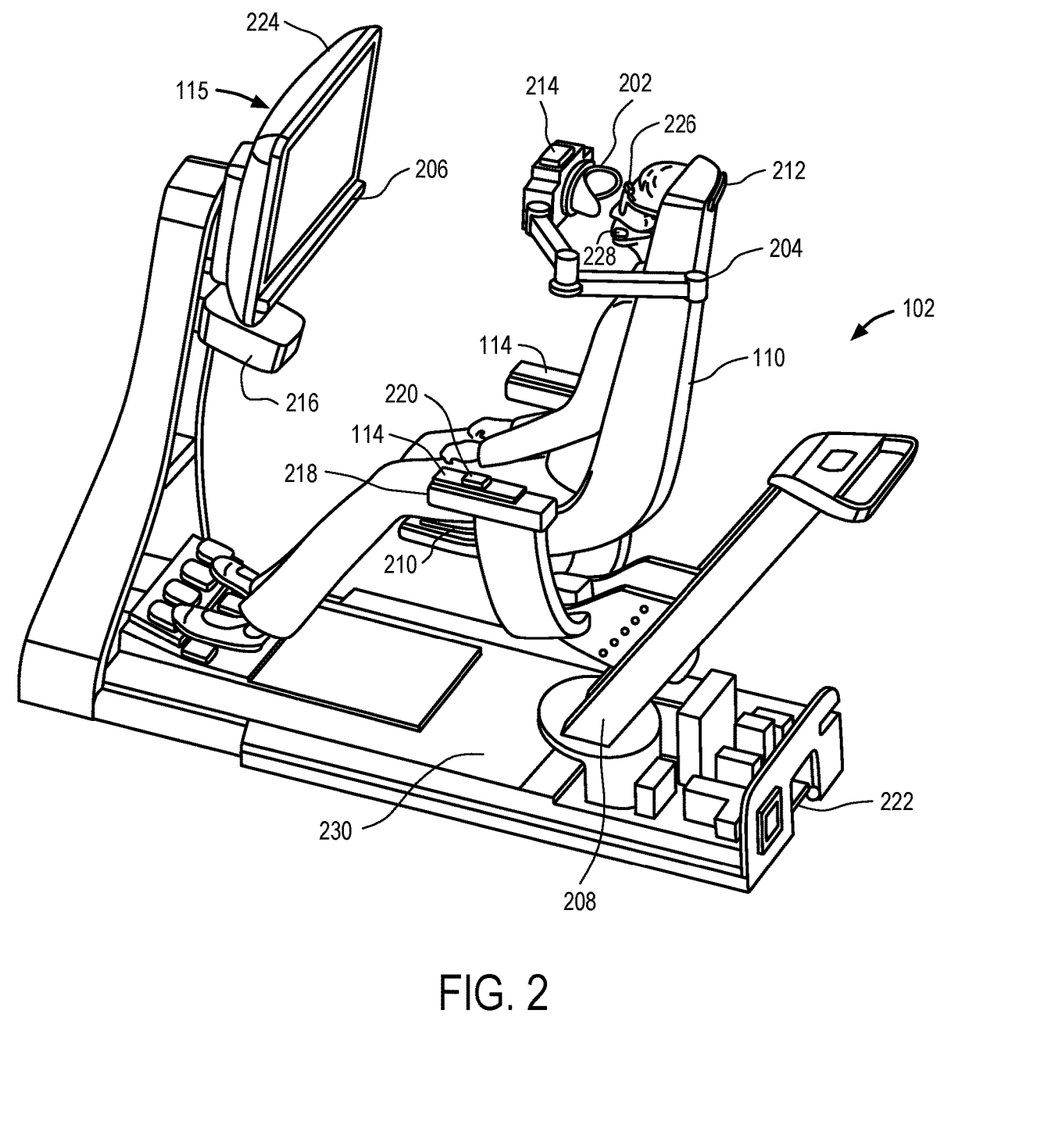
FIG. 2 is a pictorial view of a user console, in accordance with an embodiment.

Referring now to FIG. 2, FIG. 2 illustrates a pictorial view of an exemplary user console including a number of devices, mechanisms, systems and/or components used to detect whether the interlocks required for teleoperation mode are met. Representatively, user console 102 is shown including a chair 110 and display 115, as previously discussed. In addition, user console 102 is shown having an optional display 202 mounted to chair 110 by a display arm 204. For example, display 115 may be an open display, and display 202 may be an immersive display. The term "open" display is intended to refer to a display which is designed to allow the user to see outside of the display, for example with their peripheral vision, even when directly facing the display. In addition, in an open display, the user can be a distance from the display screen or not directly in front of the display, and still view a surgical procedure on the display. Therefore, in an open display such as display 115, the fact that the user may not be close to the display or have their face directly in front of the display, would not necessarily mean the user is not looking at the display or focused on the surgical procedure. In the case of an open display, in which the user can turn their head and still see the display using their peripheral vision, it is therefore important that turning of the head slightly not be interpreted to mean the user is not focused on the display. Rather, in the case of an open display, there will be some tolerance to such actions and allow for teleoperation mode to continue. This is in contrast to an immersive display such as display 202. For example, display 202 could be a completely immersive display (as in the case of a periscope) that prevents the user from seeing outside of the display screen when they are facing the display and requires the user to be relatively close to the display screen. For example, in the case of an immersive display, the user must have their face relatively close to, and facing, the display screen to use it to view the surgical procedure in progress. If the user pulls their head away from the display screen, or doesn't face the display screen, they can no longer see the display screen, therefore this would typically be interpreted to mean the user is not focused on the screen or not paying sufficient attention to continue in teleoperation mode.

To detect whether all the interlocks required for engagement of the teleoperation mode (or continuing in the teleoperation mode) are met, user console 102 may further include a number of interlock detecting devices, mechanisms, systems and/or components. The interlock detecting mechanisms may include, but are not limited to, an eye and/or head tracker 206, tracking markers 226 on the user's glasses, tracking markers 228 on the user's face mask, a chair swivel sensor 208, a chair pressure sensor 210, a headrest pressure sensor 212, an immersive display deployment sensor 214, a UID tracking sensor 216, UID storage sensor 218, UID contact sensor 220, and/or a transport sensor 222. Each of the interlock detecting mechanisms are configured to detect at least one of a number of conditions (referred to herein as "interlocks") which are required to engage the teleoperation mode. As previously discussed, the interlocks may correspond to user interactions with the user console that indicate the user is looking at, or otherwise focused on, the display, holding the controllers (e.g., UID) in a usable manner and/or the surgical environment is set up in a usable manner. Table 1 provides an exemplary listing of the specific interlocks which are required to engage a teleoperation mode, and to continue teleoperation mode, once engaged.

TABLE 1

| Interlock | Description |
| --- | --- |
| 1 | Eye tracker indicates user gaze on the display |
| 2 | Tracking marker on glasses indicates user head rotated toward the display |
| 3 | Tracking marker on a face mask indicates user head is rotated toward the display |
| 4 | Chair sensor indicates chair is facing the display |
| 5 | Chair sensor indicates user is seated in the chair |
| 6 | Chair sensor indicates user's head is resting on the headrest |
| 7 | Immersive display sensor indicates immersive display is in a use position |
| 8 | Tracker indicates UID is inside the trackable workspace |
| 9 | Tracker indicates UID trackable workspace not distorted and tracker signal is accurate |

TABLE 1-continued

| Interlock | Description |
| --- | --- |
| 10 | Tracker indicates a UID is being held by the user |
| 11 | Tracker indicates the system is not in a transportation mode |

If any of interlocks 1-11 are not detected, a teleoperation mode cannot be engaged, or if already engaged, may be automatically disengaged. Said another way, if any one or more of the following conditions listed in Table 2 are determined (e.g., when any of interlocks 1-11 are not detected) teleoperation mode is either not engaged or disengaged.

TABLE 2

| Condition | Description |
| --- | --- |
| 1 | Eye tracker indicates user gaze is outside of the display |
| 2 | Tracking marker on glasses indicates user head rotated away from the display |
| 3 | Tracking marker on a face mask indicates user head is rotated away from the display |
| 4 | Chair sensor indicates chair is facing away from the display |
| 5 | Chair sensor indicates user is not seated in the chair |
| 6 | Chair sensor indicates user's head is not resting on the headrest |
| 7 | Immersive display sensor indicates immersive display is in a non-use position |
| 8 | Tracker indicates UID is outside the trackable workspace |
| 9 | Tracker indicates UID trackable workspace distorted and tracker signal is not accurate |
| 10 | Tracker indicates a UID is not being held by the user, or is in a stored configuration |
| 11 | Tracker indicates the system is in a transportation mode |

The interlock detecting mechanisms for detecting, for example, interlocks 1-7 listed in Table 1, which generally relate to whether the user is looking at or focused on the display, may include eye and/or head tracker 206, tracking markers 226 on the user's glasses, tracking markers 228 on the user's face mask, chair swivel sensor 208, chair pressure sensor 210, headrest pressure sensor 212, and immersive display deployment sensor 214. The interlock detecting mechanisms for detecting, for example, interlocks 8-10 listed in Table 1, which generally relate to whether the user is holding the controllers in a usable manner, may include UID tracking sensor 216, UID storage sensor 218 and UID contact sensor 220. The interlock detecting mechanisms for detecting interlock 11, which relates to whether the surgical environment is set up in a usable manner, may include transport sensor 222, in addition to one or more of the UID sensors 216, 218, 220. Once a condition or interlock is detected by the interlock detecting mechanism, the information is output to a processing component of the surgical robotic system, where it is received as an interlock input and monitored to determine whether teleoperation should continue, should be engaged or should be disengaged. For example, if interlock inputs corresponding to all the required interlocks for teleoperation mode are received, teleoperation mode is engaged. If any interlocks are missing, teleoperation mode is not engaged (if currently in a non-teleoperation mode), or disengaged (if currently in teleoperation mode).

Referring now in more detail to each of the interlock detecting mechanisms, eye and/or head tracker 206 may be a tracking device that is coupled to the display 115 to track a user's gaze and/or head with respect to the display 115, and indicate whether or not the user is looking toward or away from the display. Eye and/or head tracker 206 may be attached to any portion of display 115 suitable for tracking a gaze of a user. For example, eye and/or head tracker 206 may be attached to a housing 224 of display 115, for example, a top wall, a bottom wall, or a side wall of housing 224, or integrated within a screen (not shown) mounted within the housing 224 of display 115. Eye and/or head tracker 206 may include one or more projector(s) and camera(s) which face the user and can be used to track a gaze of a user. Representatively, the projector(s) may create a pattern of near-infrared light on the eyes of the user, and the camera(s) may take images of the user's eyes and the pattern. Eye and/or head tracker 206 may further be programmed to use this information (e.g., execute machine learning, image processing and/or mathematical algorithms) to determine where the user is looking based on a position of each of the user's eyes and/or gaze point or location relative to one another, and display 115. For example, when the user is sitting on chair 110 in front of display 115, eye and/or head tracker 206 may be configured to create a pattern of near-infrared light on the eyes of the user and take images of the user's eyes and the pattern. This information may, in turn, be input to the surgical robotic system processing component (e.g., an interlock input signal) to determine whether the gaze of the user is inside or outside of display 115. If the gaze is determined to be inside the display, the user is determined to be looking toward the display. On the other hand, if the gaze is determined to be outside the display, the user is determined to be looking away from the display.

In addition, eye and/or head tracker 206 can also track a position, orientation and/or location of the user's head as an indication of whether the user is looking at the display. For example, tracker 206 may detect that the user's head is in front of the display and/or the user's face or nose is facing display 115, which suggests the user is looking at the display, or that the user's head is not in front of the display and/or their face or nose is turned away from display 115, which suggests the user is looking away from the display. In addition, the tracker 206 may be used to determine automatically if the open display 115 or the immersive display 202 should be used for teleoperation.

Still further, tracking markers 226 on the user's glasses and/or tracking markers 228 on the user's face mask may be used to determine whether the user is looking toward or away from the display 115. The tracking markers 226 on the user's glasses (e.g., 3D glasses) and/or markers 228 on the face mask (if user is sterile) may be active or passive markers. The markers 226 and/or 228 may track if the user's head is rotated toward the screen, indicating the user is looking toward the display. The markers 226 and/or 228 may further track whether the head is rotated away from the screen, indicating the user is looking away from the display. In some cases where the markers 226 are attached to the user's glasses, they may be similar to the previously discussed eye and/or head tracker and include one or more projectors, cameras and/or processing algorithms that can analyze information received from the camera(s) and projector(s) to determine whether the user is looking at the display.

Additional interlock mechanisms for detecting whether or not the user is looking toward or away from the display may include a swivel sensor 208, chair pressure sensor 210, and a headrest pressure sensor 212. The swivel sensor 208 may be any type of sensing device or component suitable for detecting a rotation (or swivel) and/or orientation of the chair 110, with respect to, for example, a stationary base 230. For example, the swivel sensor 208 may include a position encoder, switch or the like. The swivel sensor 208 may then output a corresponding signal to a processing component of the surgical robotic system corresponding to the rotation, position and/or orientation of the chair 110. The surgical robotic system can then use this information to determine whether the chair 110 is facing display 115, and therefore a user seated in the chair is facing the display 115. If, on the other hand, swivel sensor 208 detects the chair is facing away from the display, it is determined the user is looking away from the display. The chair pressure sensor 210 and the headrest pressure sensor 212 may be pressure sensors which are attached to the chair headrest and chair seat, respectively. The chair pressure sensor 210 can be used to detect when the user is seated in the chair 110, and the headrest sensor 212 can be used to detect when the user's head is resting on the headrest. Sensors 210, 212 may output a signal indicating that the user is seated in chair 110 and/or the head is resting on the headrest to the system processing component, which can be used as indicators that the user is looking at the display 115. If the sensors 210, 212 do not detect the user seated in the chair 110, this is interpreted as an indication the user is not looking toward the display, or looking away from the display. Sensors 210 and 212 may be any type of sensor suitable for detecting the user applying pressure to the seat in the particular location in which the sensor is positioned, for example, they may be pressure plates that are mounted within portions of the headrest and seat which would be contacted by a user seated in the chair 110. It should be understood, however, if chair 110 of console 102 does not swivel, swivel sensor 208 may be omitted, and interlock 4 of Table 1 (e.g., chair sensor indicates chair is facing the display) may not be required to engage teleoperation mode.

In addition, in embodiments where user console 102 includes immersive display 202, an immersive display deployment sensor 214 to detect a location of the immersive display 202 may be provided. The immersive display deployment sensor 214 may be coupled to the immersive display 202 and include switches, encoders or the like that are operable to determine if display 202 is in a "use" position (e.g., position suitable for viewing by a user seated in the chair), "non-use" position (e.g., positioned not suitable for viewing by a user seated in the chair) and/or deployed position (e.g., positioned in front of the chair). This information can be used in conjunction with a sensor (e.g., pressure or light gate sensor) to determine if the user's head is in the immersive display 202. A teleoperation mode will only be engaged if the immersive display 202 is in the "use" configuration and the sensor detects that the user's head is in the immersive display 202. If display is determined to be in "non-use" position and/or the user's head is not detected in display 202, this is interpreted as an indication the user is looking away from the display. It should be understood, however, if immersive display 202 is omitted, deployment sensor 214 may be omitted, and interlock 7 of Table 1 (e.g., immersive display sensor indicates immersive display is in a use position) is not required to engage teleoperation mode.

In addition, the interlock detecting mechanisms for detecting, for example, interlocks 8-10 listed in Table 1, which generally relate to whether a user is holding the controllers (e.g., UID) in a usable or non-usable manner or configuration, may include UID tracking sensor 216, UID storage sensor 218, and/or UID contact sensor 220. The sensor 216, 218 and/or 220 may be, for example, an optical tracker, a position tracker and/or an encoder, that is coupled to the user console and/or the UID. The sensor 216, 218 and/or 220 may be used to track, for example, the position of the UID, whether the user is holding the UID in a usable or non-usable manner, and/or whether the UID is inside or outside of the trackable workspace. If the UID is outside of the workspace, the UID is not being held in a usable manner, and the system should be disengaged. In addition, if the tracking space is distorted and the signal received from the tracker does not give an accurate reading, the UID is considered not to be in a usable manner or in a non-usable configuration, and teleoperation should be disengaged. Still further, the sensor 216, 218 and/or 220 can be used to track whether the UID is stored within the user console (e.g., within a holster or other holding mechanism) and/or the UID has been dropped. If the UID is stored within the console and/or has been dropped, such that the user is no longer holding the UID, the UID is considered to be in a non-usable configuration, and teleoperation should be disengaged. In some embodiments, one or more of sensors 216, 218, 220 may be an optical tracker and/or an absolute encoders. In some embodiments, a position sensor (optical tracker) is mounted on the user console (e.g., near display 115) and/or the base of the UID. In some embodiments, the UID is tracked by a sensor coupled to the console or the user. The position sensor can provide the position of the UID relative to a user and/or a ground reference point (not shown). In some embodiments, more than one (e.g., a plurality, several) tracking technologies are used in conjunction.

In addition, the interlock detecting mechanisms for detecting, for example, interlock 11 listed in Table 1, which generally relates to whether the surgical environment is set up in a usable manner or non-usable manner, may include transport sensor 222. Transport sensor 222 may be a sensor which detects when the surgical robotic system is transitioned to a transportation configuration or mode (e.g., console 102 can be moved), by sensing, for example, that the brakes are released. If a transition to a transportation configuration is detected, the transportation interlock is no longer met, and the surgical environment is considered to be a non-usable configuration and teleoperation mode should be disengaged. If, on the other hand, the transport sensor 222 determines the system is not in a transportation configuration (e.g., the brakes are engaged), the surgical environment is in a usable configuration, and teleoperation can be engaged.

Additional interlock detecting mechanisms may include the use of the eye tracking aspects previously discussed for determining interpupillary distance (IPD) for the immersive display 202. For example, given the position of the center of the eyeballs from the eye tracker, the IPD can be calculated for the immersive display. This may remove a requirement for the user to manually adjust the immersive display IPD.

Figure 3:
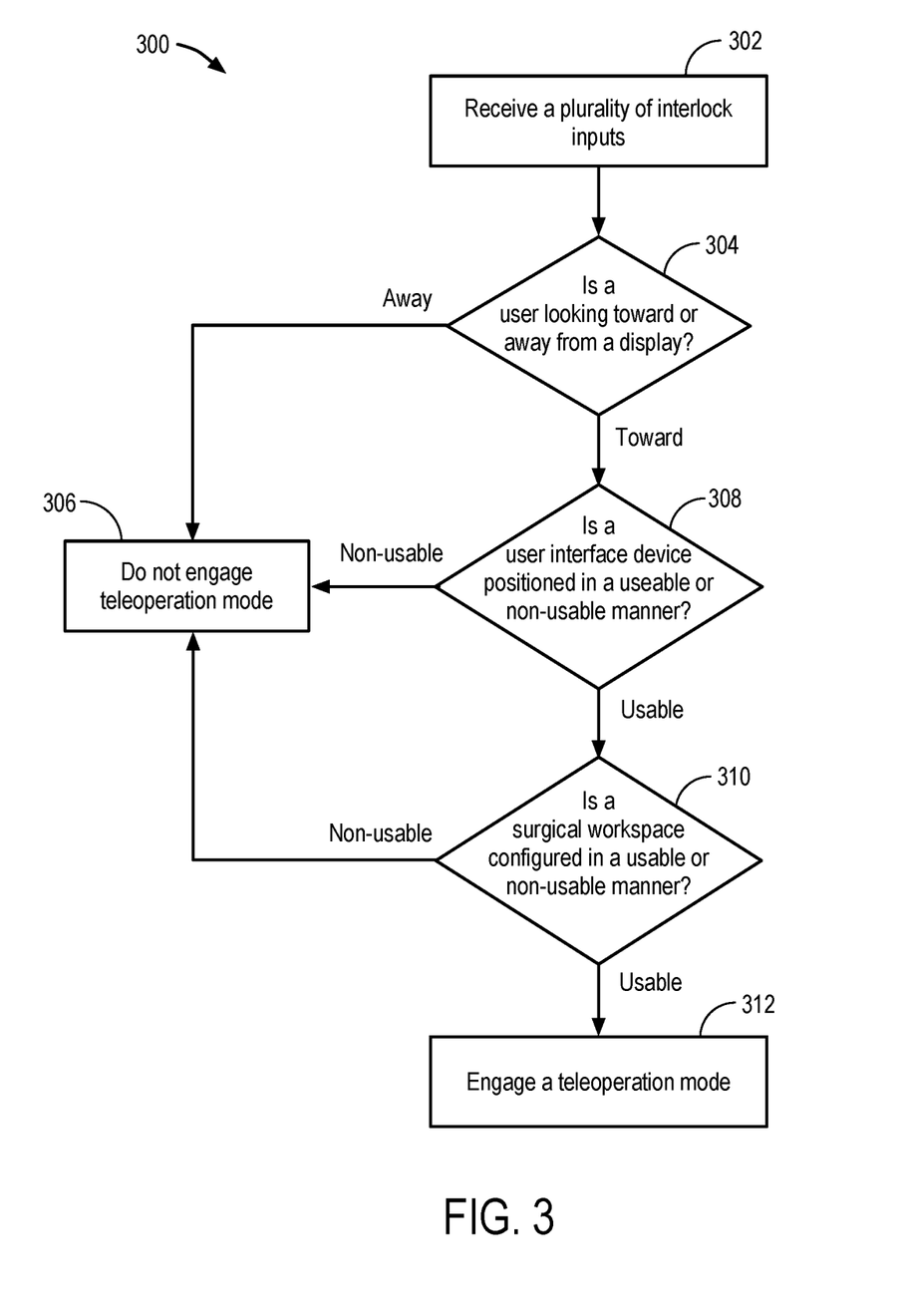
FIG. 3 is a block diagram of an exemplary operation for disengaging or engaging a teleoperation mode, in accordance with an embodiment.

FIG. 3 is a block diagram of an exemplary operation for disengaging or engaging a teleoperation mode, in accordance with an embodiment. Representatively, process 300 includes the operations of receiving a plurality of interlock inputs (block 302). The plurality of interlock inputs may be one or more of the interlocks 1-11 received from the interlock detecting mechanisms previously discussed in reference to FIG. 2 and Table 1. Based on the plurality of interlock inputs received, the system then determines whether a user is looking toward or away from the display (block 304). As previously discussed, the interlocks indicating that the user is looking toward the display may be interlocks 1-7 listed in Table 1. If any one of interlocks 1-7 are not met or satisfied, in other words at least one of conditions 1-7 listed in Table 2 is detected, it is determined that the user is not looking toward the display (e.g., looking away) and teleoperation mode is not engaged (block 306). On the other hand, if all of interlocks 1-7 listed in Table 1 are met or satisfied, it is determined at operation 304 that the user is looking toward the display and process 300 continues to operation 308.

At operation 308, the system determines whether a user interface device is positioned in a usable or non-usable manner. A user interface device is considered positioned in a usable manner when it is in a position suitable for a user to control a surgical instrument in a teleoperation mode. The user interface device may be considered to be in a non-usable manner when it is not in a position suitable for the user to control the surgical instrument. Representatively, the user interface device is considered positioned in a usable manner if all of the interlocks 8-10 listed in Table 1 are met or satisfied, and the process 300 continues to operation 310. For example, if UID 114 is inside a trackable workspace, the tracking workspace is not distorted and the UID 114 is being held by the user, the UID 114 is positioned in a usable manner. On the other hand, if it is determined at operation 308 that one of conditions 8-10 listed in Table 2 are detected, namely the UID is outside of the trackable workspace and the information received from the tracker is not accurate, the tracking space is distorted and the signal received from the tracker does not give an accurate reading, or the UID is not being held by a user (e.g., the UID is stored or dropped), the system determines the user interface device is not positioned in a usable manner, or is positioned in a non-usable manner, and does not engage teleoperation mode.

In operation 310, the system determines whether the surgical workspace is configured in a usable manner or a non-usable manner. The surgical workspace (e.g., the user console, robotic arms, surgical table, etc) may be considered to be positioned or configured in a usable manner when components of the surgical workspace are properly configured for a user to control a surgical instrument in a teleoperation mode. For example, the surgical workspace is considered to be configured in a usable manner if the interlock 11 listed in Table 1 is met or satisfied. For example, if the user console, chair, display or other associated component is in a fixed configuration (e.g., not in a transportation configuration in which the brakes are released), the surgical workspace is considered to be properly configured. If the surgical workspace is configured in a usable manner, the process continues to operation 312 and teleoperation mode is engaged. If, on the other hand, it is determined at operation 310 that the system is transitioned to a transportation configuration (e.g., the brakes are released), in other words condition 11 of Table 2 is detected, the surgical workspace is configured in a non-usable manner for teleoperation mode, and the process proceeds to operation 306 and teleoperation mode is not engaged.

Figure 4:
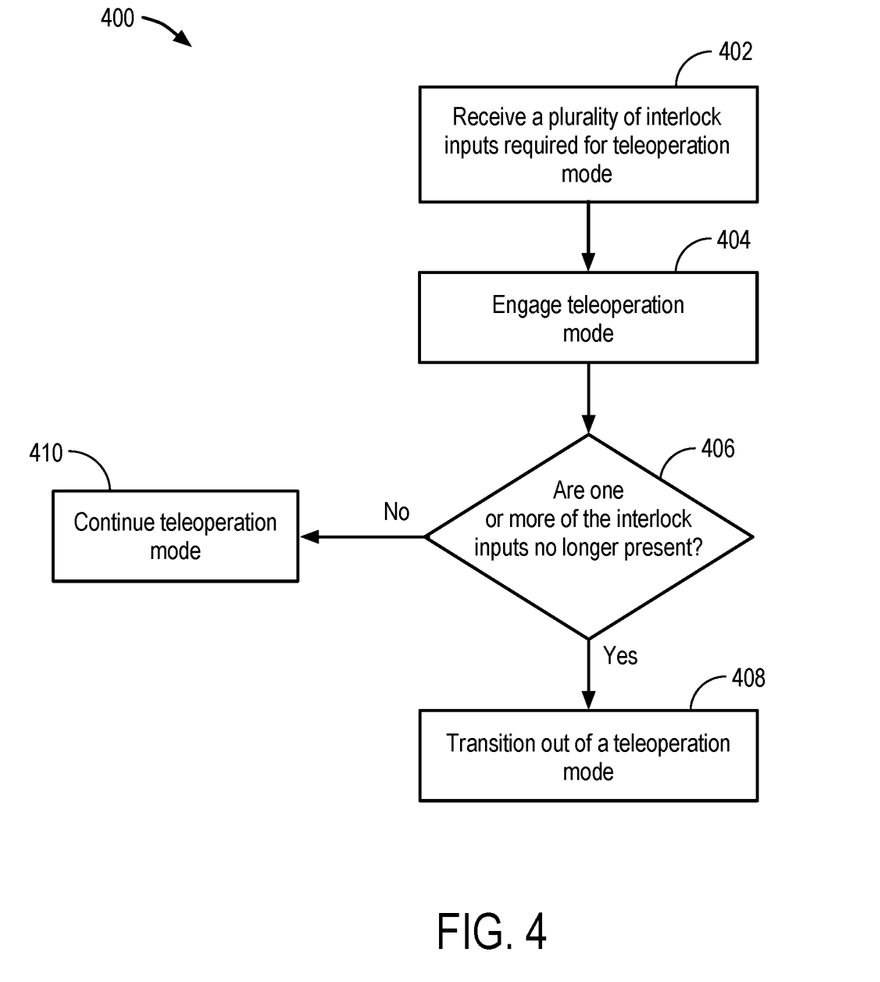
FIG. 4 is a block diagram of an exemplary operation for disengaging a teleoperation mode, in accordance with an embodiment.

FIG. 4 is a block diagram of an exemplary operation for disengaging a teleoperation mode, in accordance with an embodiment. Representatively, similarly to process 300, process 400 includes the operation of receiving a plurality of interlock inputs (block 402), for example, interlocks 1-11 previously discussed in reference to Table 1. When all of the interlock inputs required for teleoperation mode are received (e.g., the user is looking toward or otherwise focused on the display), a teleoperation mode is engaged at operation 404. Process 400 then continues to monitor whether all of the interlock inputs are still present at operation 406. As long as the interlocks continue to be detected, teleoperation mode will continue (block 410). If, on the other hand, it is determined at operation 406 that one or more of the interlock inputs is no longer detected, in other words one or more of conditions 1-11 listed in Table 2 are present, the system transitions out of the teleoperation mode at operation 408, for example to a non-teleoperation mode in which the user interface device is prevented from controlling a surgical instrument.

Figure 5:
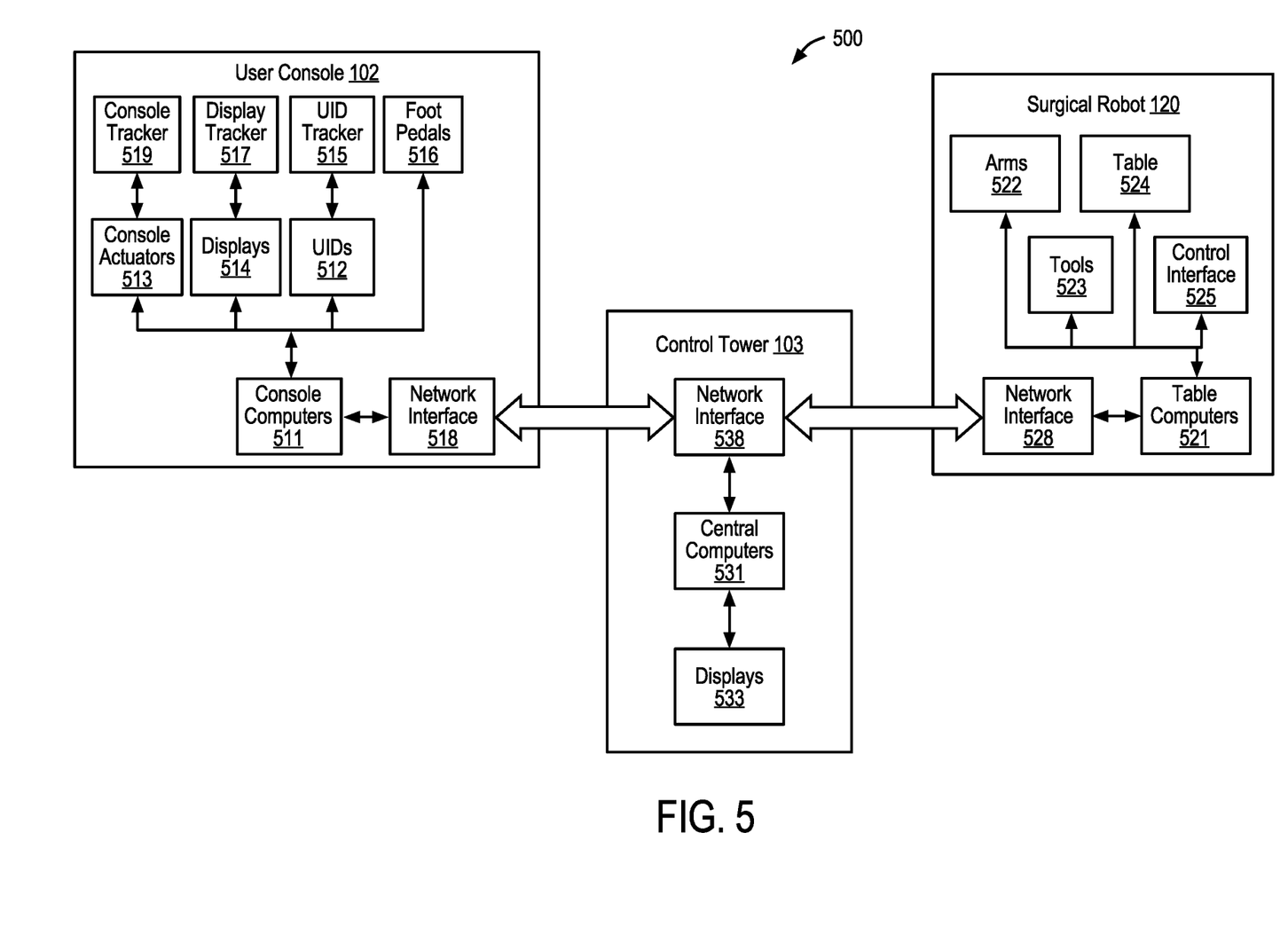
FIG. 5 is a block diagram of a computer portion of a surgical robotic system, in accordance with an embodiment.

FIG. 5 is a block diagram of a computer portion of a surgical robotic system, which is operable to implement the previously discussed operations, in accordance with an embodiment. The exemplary surgical robotic system 500 may include a user console 102, a surgical robot 120, and a control tower 103. The surgical robotic system 500 may include other or additional hardware components; thus, the diagram is provided by way of example and not a limitation to the system architecture.

As described above, the user console 102 may include console computers 511, one or more UIDs 512, console actuators 513, displays 514, foot pedals 516, console computers 511 and a network interface 518. In addition, user console 102 may include a number of interlock detecting mechanisms, devices, or components, for example, a UID tracker(s) 515, a display tracker(s) 517 and a console tracker(s) 519, for detecting whether the previously discussed interlocks required for teleoperation are satisfied. For example, UID tracker(s) 515 may include the previously discussed UID tracking sensor 216, UID storage sensor 218, and/or UID contact sensor 220. Display tracker(s) 517 may include eye and/or head tracker 206, tracking markers 226 on the user's glasses, tracking markers 228 on the user's face mask, a chair swivel sensor 208, a chair pressure sensor 210, a headrest pressure sensor 212, and/or an immersive display deployment sensor 214. Console tracker(s) may include transport sensor 222. The interlock information detected and/or tracked by any one or more of the trackers may be monitored and communicated to the console computer 511, and dispatched to the control tower 103 via the network interface 518, so that the system can determine whether to engage and/or disengage a teleoperation mode.

It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 513 based on user input or stored configurations by the console computers 511. The user may perform robot-assisted surgeries by controlling the surgical robot 120 using one or more master UIDs 512 and foot pedals 516. Positions and orientations of the UIDs 512 are continuously tracked by the UID tracker 515, and status changes are recorded by the console computers 511 as user input and dispatched to the control tower 103 via the network interface 518. Real-time surgical video of patient anatomy, instrumentation, and relevant software apps can be presented to the user on the high resolution 3D displays 514 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electro-magnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 5, the control tower 103 may include central computers 531 including at least a visualization computer, a control computer, and an auxiliary computer, various displays 533 including a team display and a nurse display, and a network interface 518 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an articulated operating table 524 with a plurality of integrated arms 522 that can be positioned over the target patient anatomy. A suite of compatible tools 523 can be attached to or detached from the distal ends of the arms 522, enabling the surgeon to perform various surgical procedures. The surgical robot 120 may also comprise control interface 525 for manual control of the arms 522, table 524, and tools 523. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 522 includes four arms mounted on both sides of the operating table 524, with two arms on each side. For certain surgical procedures, an arm mounted on one side of the table can be positioned on the other side of the table by stretching out and crossing over under the table and arms mounted on the other side, resulting in a total of three arms positioned on the same side of the table 524. The surgical tool can also comprise table computers 521 and a network interface 518, which can place the surgical robot 120 in communication with the control tower 103.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method for engaging and disengaging a surgical instrument of a surgical robotic system, the method comprising:
receiving a plurality of interlock inputs from one or more interlock detection components of the surgical robotic system, and wherein at least one of the one or more interlock detection components comprises a transport sensor for detecting whether the surgical robotic system is in a transportation mode as one of the plurality of interlock inputs;
determining, by one or more processors communicatively coupled to the interlock detection components, whether the plurality of interlock inputs indicate each of the following interlock requirements are satisfied: (1) a user is looking toward a display of the surgical robotic system, (2) at least one or more user interface devices of the surgical robotic system are configured in a usable manner, and (3) the transport sensor detects the surgical robotic system is not in the transportation mode; and
in response to determining each of the interlock requirements are satisfied, transition the surgical robotic system into a teleoperation mode in which the surgical instrument is controlled by at least one or more of the user interface devices.

2. The method of claim 1 wherein the transport sensor is coupled to a user console of the surgical robotic system and the transport sensor detects the surgical robotic system is not in the transportation mode when a brake associated with the user console is engaged.

3. The method of claim 1 wherein in response to determining less than all of the interlock requirements are satisfied, transition the surgical robotic system out of a teleoperation mode such that the at least one or more user interface devices is prevented from controlling the surgical instrument.

4. The method of claim 1, wherein the one or more user interface devices comprise at least one of a handheld user input device and a foot pedal.

5. The method of claim 1 wherein the display is an open display.

6. The method of claim 1 wherein the plurality of interlock inputs indicating a user is looking toward the display comprise:
  detecting a user gaze is toward a display of a console;
  detecting a user head is rotated toward the display;
  detecting a chair of the console is facing the display;
  detecting a user is seated on the chair; and
  detecting the display is in a use position.

7. The method of claim 1 wherein the plurality of interlock inputs indicating at least one or more user interface devices of the surgical robotic system is configured in a usable manner comprise:
  detecting at least one user interface device is inside a surgical workspace;
  detecting an accurate user interface device location is received; and
  detecting at least one user interface device is being held by the user.

8. The method of claim 1 wherein the one or more interlock detection components further comprise an eye tracker, and wherein the plurality of interlock inputs indicating a user is looking toward the display comprise the eye tracker detecting a user gaze is toward the display.

9. The method of claim 1 wherein the one or more interlock detection components further comprise a tracking marker on a user's glasses or a tracking marker on a user's face mask, and wherein the plurality of interlock inputs indicating a user is looking toward the display comprise the tracking marker indicating a user's head is rotated toward the display.

10. The method of claim 1 wherein the one or more interlock detection components further comprise a chair sensor, and wherein the plurality of interlock inputs indicating a user is looking toward the display comprise the chair sensor indicating a chair is facing the display, a user is seated in the chair or a user's head is contacting a headrest of the chair.

11. The method of claim 1 wherein the one or more interlock detection components further comprise a user interface device sensor, and at least one of the interlock requirements comprises the user interface device sensor indicating the user interface device is inside a surgical workspace, the user interface device is being held by a user or the user interface device is not in a stored position.

12. A surgical robotic system, comprising:
  a surgical instrument;
  a user console comprising a display, an interlock detecting component, and a user interface device; and
  one or more processors communicatively coupled to the interlock detecting component, the processors configured to:
  receive a plurality of interlock inputs from the interlock detecting component and transition the surgical robotic system to a teleoperation mode in which the surgical instrument is controlled by the user interface device; and
  in response to determining at least one of the plurality of interlock inputs received from the interlock detecting component is no longer present, transition the surgical robotic system out of a teleoperation mode such that the user interface device is prevented from controlling the surgical instrument, and wherein the at least one of the plurality of interlock inputs no longer present comprises a transport sensor indicating engagement of a brake associated with the user console.

13. The system of claim 12 wherein the at least one of the plurality of interlock inputs no longer present comprises an eye tracker indicating a user gaze on the display.

14. The system of claim 12 wherein the at least one of the plurality of interlock inputs no longer present comprises a tracking marker on a user's glasses or face mask indicating a head of the user is rotated toward the display.

15. The system of claim 12 wherein the at least one of the plurality of interlock inputs no longer present comprises a chair sensor indicating a chair is facing the display, a user is seated in the chair or a user's head is resting on a headrest of the chair.

16. The system of claim 12 wherein the at least one of the plurality of interlock inputs no longer present comprises a display sensor indicating the display is in a use position.

17. The system of claim 12 wherein the at least one of the plurality of interlock inputs no longer present comprises a tracker indicating the user interface device is inside a surgical workspace or the user interface device is being held by a user.

18. The system of claim 12 wherein the plurality of interlock inputs indicate each of the following interlock requirements are satisfied: (1) a user is looking toward a display of the surgical robotic system, (2) at least one or more user interfaces device of the surgical robotic system is configured in a usable manner, and (3) a surgical workspace of the surgical robotic system is configured in a usable manner.

19. The system of claim 12 wherein the one or more user interface devices comprise at least one of a handheld user input device and a foot pedal, and the display is an open display.

* * * * *